US005763252A

United States Patent [19]

Skadsen et al.

[11] Patent Number: 5,763,252
[45] Date of Patent: Jun. 9, 1998

[54] CLONED α-GLUCOSIDASE FROM BARLEY

[75] Inventors: Ronald W. Skadsen; Brian K. Tibbot, both of Madison, Wis.

[73] Assignee: Wisconsin Alumni Research Foundation, Madison, Wis.

[21] Appl. No.: 430,925

[22] Filed: Apr. 28, 1995

[51] Int. Cl.[6] .................... C12N 9/24; C12N 9/44; C12N 1/20; C07H 21/04
[52] U.S. Cl. .................. 435/200; 435/201; 435/210; 435/69.1; 435/320.1; 435/252.3; 536/23.2
[58] Field of Search ................... 435/200, 201, 435/210, 69.1, 320.1, 252.3; 536/23.2

[56] References Cited

PUBLICATIONS

Tibbot et al (1996) Plant Mol. Biol. 30:229–241. "Molecular Cloning and Characterization of a Giberellin–Inducible, Putative γ–Glucosidase From Barley".

Henson, C.A., and R.W. Skadsen, "Improved Starch Hydrolysis Using Barley Alpha–Gucosidase," Grant Application to Midwest Plant Biotechnology Consortium (1992).

Hoefsloot, L.H., et al., "Primary Structure and Processing of Lysosomal α–glucosidase: Homology with the Intestinal Sucrase–Isomaltase Complex," The EMBO J., 7:1697–1704 (1988).

Kinsella, B.T., et al., "Primary Structure and Processing of the Candida tsukubaensis α–glucosidase: Homology with the Rabbit Intestinal Sucrase–Isomaltase Complex and Human Lysosomal α–glucosidase," FEBS, (1991). Eur J Biochem 202:657–664.

Martiniuk, F., et al., "Sequence of the cDNA and 5'–Flanking Region for Human Acid α–Glucosidase, Detection of an Intron in the 5' Untranslated Leader Sequence, Definition of 18–bp Polymorphisms, and Differences with Previous cDNA and Amino Acid Sequences," DNA and Cell Biol., 9:85–94 (1990).

Naim, H.Y., et al., "Striking Structural and Functional Similarities Suggest that Intestinal Sucrase–Isomaltase, Human Lysosomal α–Glucosidase and *Schwanniomyces occidentalis* Glucoamylase are Derived from a Common Ancestral Gene," FEBS 294:100–112 (1991).

Newman, T., "380 *Arabiodopsis thaliana* cDNA Clone 38A2T7," DNA Sequence Accession No. T04333, Unpublished (1993).

Sun, Z., and C.A. Henson, "Degradation of Native Starch Granules by Barley α–Glucosidases," Plant Physiol., 94:320–327 (1990).

Sun, Z., and C.A. Henson, "A Quantitative Assessment of the Importance of Barley Seed α–Amylase, γ–Amylase, Debranching Enzyme, and α–Glucosidase in Starch Degradation," Arch. Biochem. Biophys., 284:298–305 (1991).

Svensson, B., "Regional Distant Sequence Homology Between Amylases, α–Glucosidases and Transglucanosylases," FEBS Letters, 230:72–76 (1988).

Tibbot, B.K. and R.W. Skadsen, "Cloning of A GA$_3$–Responsive Alpha–Glucosidase cDNA From the Aleurone of Germinating Barley and Analysis of Its Expression," Supplement to Plant Physiology, 105 (1994).

*Primary Examiner*—Robert A. Wax
*Assistant Examiner*—Daniel Mytelka
*Attorney, Agent, or Firm*—Quarles & Brady

[57] ABSTRACT

A cDNA clone from barley, pAGL.2737, SEQ ID NO: 3, which encodes the enzyme α-glucosidase, is disclosed. A vector and microbial host containing a DNA sequence coding for the expression of barley α-glucosidase, and a DNA construct comprising a DNA sequence coding for the expression of barley α-glucosidase, together with a promoter located 5' to the DNA coding sequence and a 3' termination sequence, are also disclosed.

7 Claims, 4 Drawing Sheets

FIG 1

```
                                1                                            50
                       r  evP             d                  v          pf            vRsg
1  Human  gluc    -RRYEVPLE..    .......TP  RVHSRAPSPL   ..........   YSVEFSEEPF  GVIVHRQLDG
2  Rabbit imal    -KRYEVPHQF.    .......VTE FAGPAATETL   ..........   YDVQVTENPF  SIKVIRKSNN
3  Rabbit suc     -KRYEVPVPL.    .....DIPA  TPTSTQENRL   ..........   YDVEIKENPF  GIQIRRRSTG
4  Sch. Oc. gamy  -.VFVLPEHLV    VKP.LVEGDA QSYN...FDN   SDLVFEY...   ....SNTDF   SFEVIRSSTK
5  Candida gluc   -QQYQLPNGLI    FDR.PGDNPA DIQNGSTADQ   SDLVFHHTAE   NGTQSGNGGW  AFWIARKSSG
6  Barley gluc    -PRWEVPQDII    PRPAPGDVLH DAPPASSAPL   QSRVLSPGSD   LVLTVHASPF  RFTVSRRSTG 100
    lfdt                       lvf           dqy     sLP    P       yGl  gEh    fr           tl
1   RVLLNT...    ............   .TVAPLFFA    DQFLQLSTSL  PSQ..YITGL  AEHL.SPLML  STSWTRITLW
2   RILFDS...    ............   ..SIGPLVYS   DQYLQISTRL  PSE..YMYGF  GEHVKRFRH   DLYWKTWPIF
3   KVIWDS...    ............   ..CLPGFAFN   DQFIQISTRL  PSE..YIYGF  GEAEHTAFKR  DLNWHTWGMF
4   EVLFSTK...   ............   ...GNPLVFS   NQFIQFNSSL  PKN.HVITGL  GESIHGLV..  NEPGSVKTLF
5   DVIFDTRASN   IPTYNDGLSS     VSSNTKRNTT   AMPAHEMVFE  NQYLQISSAL  PTG.ANIYGL  GEYVTGSFRR  NPDETLQPFF
6   DTLFDT...    ............   ............ DKYLEVTSAL  PADRASLYGL  GEHTKSSFRL  RHN.DSFTLW 150
    D       lYG  hpfy  m  r     g           ahgV ll                 vt   vig    GldfyfF G p
1   NRDLAPTPGA   N.LYGSHPFY     LALED.GGS.   ..AHGVFLLN  SPALSWRSTG  GILDVYIFLG  P.........
2   TRDQHTDDNN   NNLYGHQTFF     MCIEDTTGK.   ..SFGVFLMN  TPIVTYRVIG  GILDFYIFLG  D.........
3   TRDQPPGYKL   NS.YGFHPYY     MALED.EGN.   ..AHGVLLLN  TPALTYRVIG  GILDFYMFLG  P.........
4   ANDVGDP.ID   GNIYGVHPVY     LDQRYDTET.   ..THAVYWRT  ES.ITWRALS  GVIDLYFFSG  P.........
5   TLDAGTP.VD   SNMYGYHPIY     TEARRGSDGK   LRTHSVHLQN  GV.IQYRAIG  GTLDFRFFSG  DQPASSSSSS
6   NADIGASYVD   VNLYGSHPFY     MDVRA.PGT.   ..AHGVLLLS  SNGMDVLY.G  GSYVTYKVIG  GVLDFYFFAG  P.........

250                                                                   300
     P  vv    QY    i    Pa           pYWs Gfh         cR gY ns                vv       a iPlevw    DiDYmd kD
1   ..EPKSVVQ QYLDVVGYPFM  PPYWGLGFHL  CRWGYSSTAI  TRQVVENMTR  AHFPLDVQWN  DiDYmd kD
2   ..TPEQVVQ QYQELIGRPAM  PAYWSLGFQL  SRWNYNSLDV  VKEVRRNRE   ALIPFDTQVS  DLDYMDSRRD
3   ..TPEVATQ QYHEVIGHPVM  PPYWSLGFQL  CRYGYRNTSE  IIELYEGMVA  ADIPYDVQYT  DIDYMEDKKD
4   ..TPKDAIQ QYVKEIGLPAF  QPYWSLGYHQ  CRWGYDTIEK  LSEVVENFKK  FNIPLETIWS  DIDYMERQLD
5   SGNDKAVATV KNSPNTAIQ   HPYWSYGFHL  CRWGYNNVSE  TQAVIDAMRQ  NNIPLEVQWN  DIDYMDSYKD
6   ..NPLAVVD QYTQLIARPAP  MPYWSFGFHQ  CRYGYLNVSD  LERVVARYAK  ARIPLEVMWT  DIDYLQEFRD
                                                                            DIDYMDGFKD
```

```
                                                         350
       FT  d   f      el  fvd  l    h n q Yv  l  lDp  l            Y        f rG   d f    l        g vwp
    FTFNKDGFR. .DFPAMVQEL HQGGRRYMMI VDPAISSSGP ...AGS..YRP YDEGLRRGVF IT.NETGQPL IGKVWP.....
    FTYDRVAYN. .GLPDFVQDL HDHGQKYVII LDPAISINRR ..ASGEAYES YDRGNAQNVW VNESDGTTPI VGEVWP.....
    FTIDE.NFR. .ELPQFVDRI RGEGMRYIII LDPAISGN.. ...ETRPYPA FDRGEAKDVF VKWPNTSDIC WAKVWPDLPN
    FTYDPHRFPL DEYRKFLDEL HKNNQHYVPI LDAAIYVPNP NNATDNEYQP FHYGNETDVF LKNPDGSL.Y IGAVWQ.....
    FTTDPQRFPQ KEFAAMIAKL KDNHQHYIPI IDMAI.PKAP TNDTDVYYPG TR.GDELDVF IKNRNGSQ.Y IGEVWP.....
    FTLDRVNFTA AELRPFVDRL HRNAQKYVLI LDPGIGVDPI ..DAT..YGT FVRGMQQDIF LKRNGTN..F VGNVWP.....

400                                                                 450
              g      fpdF    p       aeW   e    f    P     dglWidMNE   S  F        at  r
    ........ ........ .GST AFPDFTN..P TALAWWEDMV AE.FHDQVPF DGMWIDMNEP SNFIRGSEDG CPNN.E....
    ........ ........ .GDT VYPDFTS..P NCIEWWANEC .NIFHQEVNY DGLWIDMNEP SSFVQGSNKG CNDNT.....
    ITIDESLTED EAVNASRAHA AFPDFFR..N STAEWWTREI LDFYNNYMKF DGLWIDMNEP SSFVNGTTTN VCRNTE....
    ........ ........ .VT LFSRFLSRKH SDMDK.....V IKDWYELTPF DGIWADMNEV SSFCVG.SCG TGKYFENPAY
    ........ ........ .G. .YTNFVDQQA ENAGKWWTEA IRNFSEIVDF SGIWLDMNEP SSFVIGNAAG PETNLSNT..
    ........ ........ GDV YFPDFMH..P AAAEFWAREI .SLFRRTIPV DGLWIDMNEI SNFYNPEPMN A.........

500
    ........ ........ ........ ........ ........ ........ ........ ........
    ........ ........ ........ ........ ........ ........ ........ ........
    ........ ........ ........ ........ ........ ........ ........ ........
    .PPFTVGSKAT SYPVGF.DVS NASEWKSIQS SISATAKTSS TSSVSSSSST IDYM...... .......NTLAPG
    PAYTAATSVA GWPQGYNNLT WGT.SGNITV NGSYTYQQGP VQNNDGSKQR RSLLLSRDED VLVQRDINVN GGNGDKFGPE
    ........ ........ ........ ........ ........ ........ ........ ........

550                                           600
       L  PPY   i   n          kt  v  avh           g v  Y       HnL G  lea       at  r
    ........ .LENPPYV PGVVG..GT. .LQAAT ICASSHQFLS T.....HYNL HNLYGLTEAI ASHRALVKA.
    ........ .LNYPPYI PDIVDKL... .MYSKT LCMDSVQYWG K.....QYDV HSLYGYSMAI ATERAVERVF
    ........ .LNYPPYF PELTKRTDG. .LHFRT MCMETEHILS DGSSVLHYDV HNLYGWSQAK PTYDALQKT.
    KGNINY... ..PPYA IYNMQGDSD. .LATHA VSPNATH... ADGTVE.YDI HNLYGYLQEN ATYHALLEVF
    DPNYQYANSS QRYLSNPPYA IHNGIHISET PLNVNLDKKT VAMEAVG... VDGQRAFYDV HNLDGTLEEQ HFYNALRDIR
    ........ ..LDDPPYR INNDGTGRP. .INNKT VRPLAVHY.. ..GGVTEYEE HNLFGLLEAR ATGRGVLRD.
```

```
                                                                              700
   g Rpfv sR  STf g Gr t  HW GDn a  W              Si        ml fglfG   p  GADiCG  Fngnt eeLC
1  RGTRPFVISR STFAGHGRYA GHWTGDVWSS WE........ QLASSV PEILQFNLLG VPLVGADVCG FLGNTSEELC
2  PNKRSFILTR STFAGSGRHA AHWLGDNTAT WE........ QMEWSI TGMLEFGLFG MPLVGADICG FLAETTEELC
3  TGKRGIVISR STYPTAGRWA GHWLGDNYAR WD........ NMDKSI IGMMEFSLFG ISYTGADICG FFNDSEYHLC
4  PNKRPFMISR STFPRAGKWT GHWGGDNTAD WAY.....AY F......SI PQAFSMGIAG LPFFGADVCG FNGNSDSELC
5  PQERPFLISR STYPGAGKFT GHWLGDNYAL WTILPGEEAY KAGAGMAQSI DGVLQFQIFG IHLIGADICG FNRNSDEELC
6  TGRRPFVLSR STFVGSGRYT AHWTGDNAAT WG........ DLRYSI NTMLSFGLFG MPMIGADICG FNGNTTEELC 750
   RW qLGaFy  PF R H       e y w     s    va R   al RY ll  Py Ytl  ea h G p aRp  l    LFLEFPKD.S
1  VRWTQLGAFY PFMRNHNSLL SLPQEPYSFS EPAQ..QAMR KALTLRYALL PHLYTLFHQA HVAGETVARP LFLEFPKD.S
2  RRWMQLGAFY PFSRNHNADG QDSLLVKSSR HYLNIRYTLL PFLYTLFYKA HAFGETVARP VLHEFYED.T
3  TRWTQLGAFY PFARNHNIQF TRRQDPVSWN QT..FVEMTR NVLNIRYTLL PYFYTQLHEI HAHGGTVIRP LMHEFFDD.R
4  SRWMQLGSFF PFYRNHNYLG AIDQEPYVWE S.....VAEATR TSMAIRYLLL PYYYTLHES HTTGLPILRA FSWQFPND.R
5  NRWMMLGAFL PFMRNHNTIG AIAQEPFRWD S.....VANASR IAINKRYEIL PSLYSHMAQS AESGEPAVRA LWYEFDEVFE
6  GRWIQLGAFY PFSRDHSAIF TVRRELYLWP S.....VAASGR KALGLRYQLL PYFYTLMYEA HMTGAPIARP LFFSYPHD.V 800                                    850
   t  vd qfl    G    lv PV  Lepg t v a  yfP    wy              v       gk v     l ap dt n
1  STWTVDHQLL WGEAALLITPV LQAGKAEVTG YFPLGTWYDL QTVPIEALGS LPPPPAAPRE PAIHSEGQWV TLPAPLDTIN
2  NSWVEDREFL WGPALLITPV LTQGAETVSA YIPDAVWYDY ET........ ........ AKRPWRKQRV EMSLPADKIG
3  TTWDIFLQFL WGPAFMVTPV LEPYTTVVRG YVPNARWFDY HT........ ........G EDIGIRGQVQ DLTLLMNAIN
4  SLSGVDNQFF VGDGLVVTPV LEPGVDKVKG VFPGAGKEEV YYDWYTQR.. ........ EVHFKDGKNE TLDAPLGHIP
5  QTKDYAHQFL FGDDLLVSPV LFPNAGGKWR NVFSYEAL.. ........ DVEY..NKNV TVDAALSTIN
6  ATYGVDRQFL LGRGVLVSPV LEPGPTTVDA YFPGGRWYRL YDYSL..... ........ AVATRTGKHV RLPAPADTVN 900
   vHl gG ilp   q       r    L      val  dg A    g lfldDG-
1  VHLRAGYIIP LQ.GPGLTTT ESRQQPMALA VALTKGGEAR GELFWDDG-
2  LHLRGGYIIP IQ.QPAVTTT ASRMNPLGLI IALNDDNTAV GDFFWDDG-
3  LHVRGGHILP CQ.EPARTTF LSRQKYMKLI VAADDNHMAQ GSLFWDDG-
4  LHIRGGNVLP TQ.EPGYTVA ESRQNPFGLI VALDNDGKAQ GSLYLDDG-
5  LHLRPGKVLL THSKPAYTVY ETAQSPYGLI VNLNDQGEAK QTFYLDDG-
6  VHLTGGTILP LQ.QSALTTS RARRTAFHLL VALAEDGTAS GYLFLDDG-
```

FIG 2C

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "Oligonucleotide 4HR-AS complementary to conserved catalytic region (WIDMNE) of
family 31 members"

(x i) SEQUENCE DESCRIPTION: SEQ ID NO:1:

YTCRTTCATR TCDATCCA    18

(2) INFORMATION FOR SEQ ID NO:2:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Oligonucleotide MalG-S
encoding conserved region (GEVWPG) of family 31 members
located upstream of the conserved catalytic region"

(x i) SEQUENCE DESCRIPTION: SEQ ID NO:2:

GGNGARGTNT GGCCNGG    17

(2) INFORMATION FOR SEQ ID NO:3:

(i) SEQUENCE CHARACTERISTICS:
(A) LENGTH: 2752 base pairs
(B) TYPE: nucleic acid
(C) STRANDEDNESS: double
(D) TOPOLOGY: linear (i i) MOLECULE TYPE: cDNA (i x) FEATURE:
(A) NAME/KEY: CDS
(B) LOCATION: 42..2675

(x i) SEQUENCE DESCRIPTION: SEQ ID NO:3:

| GCGCAAGACC | GTCACACACA | CACACACACC | AGCCCCATCC | G | ATG | GCG | ACG | GTC | 53 |
| | | | | | Met | Ala | Thr | Val | |
| | | | | | 1 | | | | |

| GGG | GTG | CTG | CTG | CTC | TGC | TTG | TGT | CTC | TGC | TTA | TTC | GCG | CCC | CGC | CTG | 101 |
|---|---|---|---|---|---|---|---|---|---|---|---|---|---|---|---|---|
| Gly | Val | Leu | Leu | Leu | Cys | Leu | Cys | Leu | Cys | Leu | Phe | Ala | Pro | Arg | Leu | |
| 5 | | | | | 10 | | | | | 15 | | | | | 20 | |

| TGC | TCG | TCC | AAG | GAG | GAG | GGG | CCG | CTC | GCC | GCC | CGT | ACC | GTG | TTA | GCC | 149 |
| Cys | Ser | Ser | Lys | Glu | Glu | Gly | Pro | Leu | Ala | Ala | Arg | Thr | Val | Leu | Ala | |
| | | | 25 | | | | | 30 | | | | | | 35 | | |

| GTC | GCG | GTG | ACT | ATG | GAG | GGC | GCG | CTG | CGC | GCC | GAG | GCA | GCG | ACC | GGC | 197 |
| Val | Ala | Val | Thr | Met | Glu | Gly | Ala | Leu | Arg | Ala | Glu | Ala | Ala | Thr | Gly | |
| | | | 40 | | | | | 45 | | | | | 50 | | | |

| GGC | CGC | TCG | TCC | ACC | GGC | GAC | GTG | CAG | AGG | CTG | GCC | GTG | TAC | GCC | AGC | 245 |
| Gly | Arg | Ser | Ser | Thr | Gly | Asp | Val | Gln | Arg | Leu | Ala | Val | Tyr | Ala | Ser | |
| | | 55 | | | | | 60 | | | | | 65 | | | | |

| CTC | GAG | ACG | GAC | AGC | CGC | CTG | CGG | GTG | CGC | ATC | ACC | GAC | GCC | GAC | CAC | 293 |
| Leu | Glu | Thr | Asp | Ser | Arg | Leu | Arg | Val | Arg | Ile | Thr | Asp | Ala | Asp | His | |
| | 70 | | | | | 75 | | | | | 80 | | | | | |

| CCG | CGA | TGG | GAG | GTG | CCG | CAA | GAC | ATC | ATC | CCG | CGC | CCC | GCG | CCG | GGG | 341 |
| Pro | Arg | Trp | Glu | Val | Pro | Gln | Asp | Ile | Ile | Pro | Arg | Pro | Ala | Pro | Gly | |
| 85 | | | | | 90 | | | | | 95 | | | | | 100 | |

| GAC | GTC | CTC | CAC | GAC | GCG | CCG | CCC | GCC | TCC | TCG | GCG | CCA | CTC | CAG | GGC | 389 |
| Asp | Val | Leu | His | Asp | Ala | Pro | Pro | Ala | Ser | Ser | Ala | Pro | Leu | Gln | Gly | |
| | | | 105 | | | | | 110 | | | | | 115 | | | |

| CGG | GTC | CTC | TCC | CCC | GCG | GGC | TCG | GAC | CTC | GTG | CTC | ACC | GTC | CAC | GCC | 437 |
| Arg | Val | Leu | Ser | Pro | Ala | Gly | Ser | Asp | Leu | Val | Leu | Thr | Val | His | Ala | |
| | | | 120 | | | | | 125 | | | | | 130 | | | |

| TCC | CCG | TTC | CGC | TTC | ACC | GTC | TCC | CGC | CGC | TCC | ACC | GGC | GAC | ACC | CTC | 485 |
| Ser | Pro | Phe | Arg | Phe | Thr | Val | Ser | Arg | Arg | Ser | Thr | Gly | Asp | Thr | Leu | |

-continued

| | | | | 135 | | | | 140 | | | | 145 | | | |
|---|---|---|---|---|---|---|---|---|---|---|---|---|---|---|---|

```
TTC GAC ACC GCC CCC GGC CTC GTC TTC AGG GAC AAG TAC CTG GAG GTG    533
Phe Asp Thr Ala Pro Gly Leu Val Phe Arg Asp Lys Tyr Leu Glu Val
    150             155                 160

ACG TCG GCC CTG CCG GCG GGC CGT GCC TCC CTG TAC GGG CTG GGC GAG    581
Thr Ser Ala Leu Pro Ala Gly Arg Ala Ser Leu Tyr Gly Leu Gly Glu
165             170                 175                 180

CAC ACG AAG AGC TCG TTC CGG CTG CGG CAC AAC GAC TCC TTC ACG CTC    629
His Thr Lys Ser Ser Phe Arg Leu Arg His Asn Asp Ser Phe Thr Leu
                185                 190                 195

TGG AAC GCC GAC ATC GGC GCG TCC TAC GTG GAC GTC AAC CTC TAC GGC    677
Trp Asn Ala Asp Ile Gly Ala Ser Tyr Val Asp Val Asn Leu Tyr Gly
            200                 205                 210

TCG CAC CCC TTC TAC ATG GAC GTG CGG GCA CCG GGG ACC GCG CAC GGC    725
Ser His Pro Phe Tyr Met Asp Val Arg Ala Pro Gly Thr Ala His Gly
        215                 220                 225

GTG CTC CTG CTC AGT AGC AAC GGC ATG GAC GTG CTC TAC GGC GGG TCC    773
Val Leu Leu Leu Ser Ser Asn Gly Met Asp Val Leu Tyr Gly Gly Ser
    230                 235                 240

TAC GTC ACC TAC AAG GTC ATC GGG GGC GTC CTC GAC TTC TAC TTC TTC    821
Tyr Val Thr Tyr Lys Val Ile Gly Gly Val Leu Asp Phe Tyr Phe Phe
245                 250                 255                 260

GCC GGC CCC AAC CCC CTC GCC GTC GTC GAC CAG TAC ACC CAG CTC ATC    869
Ala Gly Pro Asn Pro Leu Ala Val Val Asp Gln Tyr Thr Gln Leu Ile
                265                 270                 275

GCC CGC CCT GCC CCA ATG CCG TAC TGG TCC TTC GGG TTC CAC CAG TGC    917
Ala Arg Pro Ala Pro Met Pro Tyr Trp Ser Phe Gly Phe His Gln Cys
            280                 285                 290

CGG TAC GGG TAC CTG AAC GTG TCT GAC CTG GAG CGT GTG GTG GCC CGA    965
Arg Tyr Gly Tyr Leu Asn Val Ser Asp Leu Glu Arg Val Val Ala Arg
        295                 300                 305

TAC GCC AAG GCC CGG ATC CCG CTG GAG GTG ATG TGG ACC GAT ATC GAC    1013
Tyr Ala Lys Ala Arg Ile Pro Leu Glu Val Met Trp Thr Asp Ile Asp
    310                 315                 320

TAC ATG GAC GGG TTC AAG GAC TTC ACC TTG GAC CGT GTC AAC TTC ACC    1061
Tyr Met Asp Gly Phe Lys Asp Phe Thr Leu Asp Arg Val Asn Phe Thr
325                 330                 335                 340

GCC GCC GAG CTC CGG CCG TTC GTC GAC CGG CTT CAC CGG AAC GCC CAG    1109
Ala Ala Glu Leu Arg Pro Phe Val Asp Arg Leu His Arg Asn Ala Gln
                345                 350                 355

AAA TAC GTC CTC ATC CTA GAC CCA GGG ATC CGG GTG GAC CCC ATC GAC    1157
Lys Tyr Val Leu Ile Leu Asp Pro Gly Ile Arg Val Asp Pro Ile Asp
            360                 365                 370

GCG ACG TAC GGG ACG TTC GTC CGC GGG ATG CAG CAG GAC ATC TTC CTG    1205
Ala Thr Tyr Gly Thr Phe Val Arg Gly Met Gln Gln Asp Ile Phe Leu
        375                 380                 385

AAG CGG AAC GGC ACA AAC TTC GTC GGC AAC GTG TGG CCG GGC GAC GTC    1253
Lys Arg Asn Gly Thr Asn Phe Val Gly Asn Val Trp Pro Gly Asp Val
    390                 395                 400

TAC TTC CCG GAC TTC ATG CAC CCA GCC GCC GCC GAG TTC TGG GCG CGG    1301
Tyr Phe Pro Asp Phe Met His Pro Ala Ala Ala Glu Phe Trp Ala Arg
405                 410                 415                 420

GAG ATC TCC CTC TTC CGC CGG ACC ATC CCG GTC GAC GGG CTG TGG ATC    1349
Glu Ile Ser Leu Phe Arg Arg Thr Ile Pro Val Asp Gly Leu Trp Ile
                425                 430                 435

GAC ATG AAC GAG ATC TCC AAC TTC TAC AAC CCG GAG CCC ATG AAC GCG    1397
Asp Met Asn Glu Ile Ser Asn Phe Tyr Asn Pro Glu Pro Met Asn Ala
            440                 445                 450

CTC GAC GAC CCG CCG TAC CGG ATC AAC AAC GAC GGG ACG GGC CGC CCC    1445
Leu Asp Asp Pro Pro Tyr Arg Ile Asn Asn Asp Gly Thr Gly Arg Pro
```

|   |   |   |   |   | 455 |   |   |   |   | 460 |   |   |   |   | 465 |   |   |   |   |      |
|---|---|---|---|---|-----|---|---|---|---|-----|---|---|---|---|-----|---|---|---|---|------|
| ATC | AAC | AAC | AAG | ACG | GTG | CGC | CCG | CTC | GCC | GTG | CAC | TAC | GGG | GGG | GTC | | | | | 1493 |
| Ile | Asn | Asn | Lys | Thr | Val | Arg | Pro | Leu | Ala | Val | His | Tyr | Gly | Gly | Val | | | | |      |
|     | 470 |     |     |     | 475 |     |     |     |     | 480 |     |     |     |     |     | | | | |      |

| ACC | GAG | TAC | GAG | GAG | CAC | AAC | CTG | TTC | GGC | CTC | CTC | GAG | GCC | CGC | GCC | 1541 |
|-----|-----|-----|-----|-----|-----|-----|-----|-----|-----|-----|-----|-----|-----|-----|-----|------|
| Thr | Glu | Tyr | Glu | Glu | His | Asn | Leu | Phe | Gly | Leu | Leu | Glu | Ala | Arg | Ala |      |
| 485 |     |     |     |     | 490 |     |     |     |     | 495 |     |     |     |     | 500 |      |

| ACG | GGG | CGC | GGG | GTG | CTG | AGG | GAC | ACC | GGC | CGC | CGC | CCC | TTC | GTG | CTC | 1589 |
| Thr | Gly | Arg | Gly | Val | Leu | Arg | Asp | Thr | Gly | Arg | Arg | Pro | Phe | Val | Leu |      |
|     |     |     |     | 505 |     |     |     |     | 510 |     |     |     |     | 515 |     |      |

| AGC | AGG | TCC | ACC | TTC | GTG | GGC | TCG | GGG | CGC | TAC | ACC | GCT | TAC | TGG | ACT | 1637 |
| Ser | Arg | Ser | Thr | Phe | Val | Gly | Ser | Gly | Arg | Tyr | Thr | Ala | Tyr | Trp | Thr |      |
|     |     |     | 520 |     |     |     | 525 |     |     |     |     |     | 530 |     |     |      |

| GGC | GAC | AAC | GCC | GCA | ACG | TGG | GGC | GAC | CTG | CGC | TAC | TCC | ATC | AAC | ACC | 1685 |
| Gly | Asp | Asn | Ala | Ala | Thr | Trp | Gly | Asp | Leu | Arg | Tyr | Ser | Ile | Asn | Thr |      |
|     |     | 535 |     |     |     | 540 |     |     |     |     | 545 |     |     |     |     |      |

| ATG | CTC | AGC | TTC | GGC | CTC | TTC | GGC | ATG | CCC | ATG | ATC | GGC | GCC | GAC | ATC | 1733 |
| Met | Leu | Ser | Phe | Gly | Leu | Phe | Gly | Met | Pro | Met | Ile | Gly | Ala | Asp | Ile |      |
|     | 550 |     |     |     |     | 555 |     |     |     |     | 560 |     |     |     |     |      |

| TGC | GGG | TTC | AAC | GGC | AAC | ACG | ACA | GAG | GAG | CTC | TGC | GGT | CGG | TGG | ATC | 1781 |
| Cys | Gly | Phe | Asn | Gly | Asn | Thr | Thr | Glu | Glu | Leu | Cys | Gly | Arg | Trp | Ile |      |
| 565 |     |     |     |     | 570 |     |     |     |     | 575 |     |     |     |     | 580 |      |

| CAG | CTC | GGA | GCC | TTC | TAC | CCC | TTC | TCG | AGG | GAC | CAC | TCG | GCG | ATC | TTC | 1829 |
| Gln | Leu | Gly | Ala | Phe | Tyr | Pro | Phe | Ser | Arg | Asp | His | Ser | Ala | Ile | Phe |      |
|     |     |     |     | 585 |     |     |     |     | 590 |     |     |     |     | 595 |     |      |

| ACC | GTC | CGG | CGA | GAG | TTG | TAC | CTG | TGG | CCG | TCG | GTG | GCG | GCG | TCG | GGC | 1877 |
| Thr | Val | Arg | Arg | Glu | Leu | Tyr | Leu | Trp | Pro | Ser | Val | Ala | Ala | Ser | Gly |      |
|     |     |     | 600 |     |     |     |     | 605 |     |     |     |     | 610 |     |     |      |

| AGG | AAG | GCG | CTC | GGG | CTC | CGG | TAC | CAG | CTG | CTC | CCT | TAC | TTC | TAC | ACG | 1925 |
| Arg | Lys | Ala | Leu | Gly | Leu | Arg | Tyr | Gln | Leu | Leu | Pro | Tyr | Phe | Tyr | Thr |      |
|     |     |     | 615 |     |     |     |     | 620 |     |     |     |     | 625 |     |     |      |

| CTC | ATG | TAC | GAG | GCG | CAC | ATG | ACG | GGG | GCG | CCA | ATC | GCG | CGG | CCG | CTC | 1973 |
| Leu | Met | Tyr | Glu | Ala | His | Met | Thr | Gly | Ala | Pro | Ile | Ala | Arg | Pro | Leu |      |
|     | 630 |     |     |     |     | 635 |     |     |     |     | 640 |     |     |     |     |      |

| TTC | TTC | TCC | TAC | CCG | CAC | GAC | GTC | GCC | ACG | TAC | GGC | GTG | GAC | AGA | CAG | 2021 |
| Phe | Phe | Ser | Tyr | Pro | His | Asp | Val | Ala | Thr | Tyr | Gly | Val | Asp | Arg | Gln |      |
| 645 |     |     |     |     | 650 |     |     |     |     | 655 |     |     |     |     | 660 |      |

| TTC | CTG | CTC | GGC | CGC | GGG | GTC | CTC | GTT | TCG | CCG | GTG | CTC | GAG | CCG | GGC | 2069 |
| Phe | Leu | Leu | Gly | Arg | Gly | Val | Leu | Val | Ser | Pro | Val | Leu | Glu | Pro | Gly |      |
|     |     |     |     | 665 |     |     |     |     | 670 |     |     |     |     | 675 |     |      |

| CCG | ACA | ACC | GTC | GAC | GCC | TAC | TTC | CCG | GCG | GGC | CGG | TGG | TAC | AGA | CTC | 2117 |
| Pro | Thr | Thr | Val | Asp | Ala | Tyr | Phe | Pro | Ala | Gly | Arg | Trp | Tyr | Arg | Leu |      |
|     |     |     | 680 |     |     |     |     | 685 |     |     |     |     | 690 |     |     |      |

| TAC | GAC | TAC | TCC | CTC | GCC | GTC | GCC | ACG | CGG | ACC | GGC | AAG | CAC | GTC | AGG | 2165 |
| Tyr | Asp | Tyr | Ser | Leu | Ala | Val | Ala | Thr | Arg | Thr | Gly | Lys | His | Val | Arg |      |
|     |     | 695 |     |     |     |     | 700 |     |     |     |     | 705 |     |     |     |      |

| CTG | CCG | GCG | CCG | GCC | GAC | ACG | GTG | AAC | GTG | CAC | CTG | ACC | GGC | GGC | ACC | 2213 |
| Leu | Pro | Ala | Pro | Ala | Asp | Thr | Val | Asn | Val | His | Leu | Thr | Gly | Gly | Thr |      |
|     | 710 |     |     |     |     | 715 |     |     |     |     | 720 |     |     |     |     |      |

| ATC | CTC | CCG | CTG | CAG | CAG | AGC | GCG | CTG | ACT | ACG | TCG | CGC | GCG | CGC | CGG | 2261 |
| Ile | Leu | Pro | Leu | Gln | Gln | Ser | Ala | Leu | Thr | Thr | Ser | Arg | Ala | Arg | Arg |      |
| 725 |     |     |     | 730 |     |     |     |     | 735 |     |     |     |     | 740 |     |      |

| ACC | GCG | TTC | CAC | CTC | CTG | GTC | GCG | CTC | GCG | GAG | GAC | GGG | ACG | GCC | AGC | 2309 |
| Thr | Ala | Phe | His | Leu | Leu | Val | Ala | Leu | Ala | Glu | Asp | Gly | Thr | Ala | Ser |      |
|     |     |     |     | 745 |     |     |     |     | 750 |     |     |     |     | 755 |     |      |

| GGC | TAC | CTT | TTC | CTG | GAC | GAC | GGC | GAC | TCG | CCG | GAG | TAT | GGC | AGG | AGA | 2357 |
| Gly | Tyr | Leu | Phe | Leu | Asp | Asp | Gly | Asp | Ser | Pro | Glu | Tyr | Gly | Arg | Arg |      |
|     |     |     |     | 760 |     |     |     |     | 765 |     |     |     |     | 770 |     |      |

| AGC | GAT | TGG | AGC | ATG | GTA | AGG | TTC | AAC | TAC | AAG | ATA | CCA | AAC | AAC | AAA | 2405 |
| Ser | Asp | Trp | Ser | Met | Val | Arg | Phe | Asn | Tyr | Lys | Ile | Pro | Asn | Asn | Lys |      |

-continued

```
                  775                         780                        785
GGG GCC ATC AAG GTG AAG TCG GAG GTG GTG CAC AAC TCG TAC GCA CAG          2453
Gly Ala Ile Lys Val Lys Ser Glu Val Val His Asn Ser Tyr Ala Gln
    790                 795                 800

AGC AGG ACA CTG GTC ATA AGC AAG GTG GTG CTC ATG GGG CAC CGG TCG          2501
Ser Arg Thr Leu Val Ile Ser Lys Val Val Leu Met Gly His Arg Ser
805                 810                 815                 820

CCG GCG GCG CCG AAG AAG CTC ACC GTC CAC GTC AAC AGC GCG GAG GTG          2549
Pro Ala Ala Pro Lys Lys Leu Thr Val His Val Asn Ser Ala Glu Val
                825                 830                 835

GAG GCG AGC TCG TCA GCC GGC ACA CGG TAC CAG AAC GCA GGA GGA CTC          2597
Glu Ala Ser Ser Ser Ala Gly Thr Arg Tyr Gln Asn Ala Gly Gly Leu
            840                 845                 850

GGC GGC GTC GCT CAC ATC GGC GGT CTG TCG CTG GTC GTC GGG GAG GAG          2645
Gly Gly Val Ala His Ile Gly Gly Leu Ser Leu Val Val Gly Glu Glu
        855                 860                 865

TTC GAA CTG AAG GTC GCC ATG TCC TAT TAA ATTTAGGCAA TTTGTGATAT            2695
Phe Glu Leu Lys Val Ala Met Ser Tyr *
    870                 875

GGACCATAAC ATTGATTGAA TAAAGGCGAG AAATTAAAGC CCAAAAAAAA AAAAAA            2752
```

( 2 ) INFORMATION FOR SEQ ID NO:4:

( i ) SEQUENCE CHARACTERISTICS:
        ( A ) LENGTH: 877 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

```
Met Ala Thr Val Gly Val Leu Leu Leu Cys Leu Cys Leu Cys Leu Phe
 1               5                  10                  15

Ala Pro Arg Leu Cys Ser Ser Lys Glu Glu Gly Pro Leu Ala Ala Arg
                20                  25                  30

Thr Val Leu Ala Val Ala Val Thr Met Glu Gly Ala Leu Arg Ala Glu
            35                  40                  45

Ala Ala Thr Gly Gly Arg Ser Ser Thr Gly Asp Val Gln Arg Leu Ala
        50                  55                  60

Val Tyr Ala Ser Leu Glu Thr Asp Ser Arg Leu Arg Val Arg Ile Thr
65                  70                  75                  80

Asp Ala Asp His Pro Arg Trp Glu Val Pro Gln Asp Ile Ile Pro Arg
                85                  90                  95

Pro Ala Pro Gly Asp Val Leu His Asp Ala Pro Ala Ser Ser Ala
            100                 105                 110

Pro Leu Gln Gly Arg Val Leu Ser Pro Ala Gly Ser Asp Leu Val Leu
        115                 120                 125

Thr Val His Ala Ser Pro Phe Arg Phe Thr Val Ser Arg Arg Ser Thr
    130                 135                 140

Gly Asp Thr Leu Phe Asp Thr Ala Pro Gly Leu Val Phe Arg Asp Lys
145                 150                 155                 160

Tyr Leu Glu Val Thr Ser Ala Leu Pro Ala Gly Arg Ala Ser Leu Tyr
                165                 170                 175

Gly Leu Gly Glu His Thr Lys Ser Ser Phe Arg Leu Arg His Asn Asp
            180                 185                 190

Ser Phe Thr Leu Trp Asn Ala Asp Ile Gly Ala Ser Tyr Val Asp Val
        195                 200                 205

Asn Leu Tyr Gly Ser His Pro Phe Tyr Met Asp Val Arg Ala Pro Gly
```

|     |     |     |     |     |     |     |     |     |     |     |     |     |     |     |
| --- | --- | --- | --- | --- | --- | --- | --- | --- | --- | --- | --- | --- | --- | --- |
|     |     |     | 210 |     |     |     | 215 |     |     |     | 220 |     |     |     |
| Thr 225 | Ala | His | Gly | Val 230 | Leu | Leu | Ser | Ser 235 | Asn | Gly | Met | Asp | Val | Leu 240 |
| Tyr | Gly | Gly | Ser | Tyr 245 | Val | Thr | Tyr | Lys 250 | Val | Ile | Gly | Gly | Val | Leu 255 | Asp |
| Phe | Tyr | Phe | Phe 260 | Ala | Gly | Pro | Asn | Pro 265 | Leu | Ala | Val | Val | Asp 270 | Gln | Tyr |
| Thr | Gln | Leu 275 | Ile | Ala | Arg | Pro | Ala 280 | Pro | Met | Pro | Tyr | Trp 285 | Ser | Phe | Gly |
| Phe | His 290 | Gln | Cys | Arg | Tyr | Gly 295 | Tyr | Leu | Asn | Val | Ser 300 | Asp | Leu | Glu | Arg |
| Val 305 | Val | Ala | Arg | Tyr | Lys 310 | Ala | Arg | Ile | Pro | Leu 315 | Glu | Val | Met | Trp 320 |
| Thr | Asp | Ile | Asp | Tyr 325 | Met | Asp | Gly | Phe | Lys 330 | Asp | Phe | Thr | Leu | Asp 335 | Arg |
| Val | Asn | Phe | Thr 340 | Ala | Ala | Glu | Leu | Arg 345 | Pro | Phe | Val | Asp | Arg 350 | Leu | His |
| Arg | Asn | Ala 355 | Gln | Lys | Tyr | Val | Leu 360 | Ile | Leu | Asp | Pro | Gly 365 | Ile | Arg | Val |
| Asp | Pro 370 | Ile | Asp | Ala | Thr | Tyr 375 | Gly | Thr | Phe | Val | Arg 380 | Gly | Met | Gln | Gln |
| Asp 385 | Ile | Phe | Leu | Lys | Arg 390 | Asn | Gly | Thr | Asn | Phe 395 | Val | Gly | Asn | Val | Trp 400 |
| Pro | Gly | Asp | Val | Tyr 405 | Phe | Pro | Asp | Phe | Met 410 | His | Pro | Ala | Ala | Ala 415 | Glu |
| Phe | Trp | Ala | Arg 420 | Glu | Ile | Ser | Leu | Phe 425 | Arg | Arg | Thr | Ile | Pro 430 | Val | Asp |
| Gly | Leu | Trp 435 | Ile | Asp | Met | Asn | Glu 440 | Ile | Ser | Asn | Phe | Tyr 445 | Asn | Pro | Glu |
| Pro | Met 450 | Asn | Ala | Leu | Asp | Asp 455 | Pro | Pro | Tyr | Arg | Ile 460 | Asn | Asn | Asp | Gly |
| Thr 465 | Gly | Arg | Pro | Ile | Asn 470 | Asn | Lys | Thr | Val | Arg 475 | Pro | Leu | Ala | Val | His 480 |
| Tyr | Gly | Gly | Val | Thr 485 | Glu | Tyr | Glu | Glu 490 | His | Asn | Leu | Phe | Gly 495 | Leu | Leu |
| Glu | Ala | Arg | Ala 500 | Thr | Gly | Arg | Gly | Val 505 | Leu | Arg | Asp | Thr | Gly 510 | Arg | Arg |
| Pro | Phe | Val 515 | Leu | Ser | Arg | Ser | Thr 520 | Phe | Val | Gly | Ser | Gly 525 | Arg | Tyr | Thr |
| Ala | Tyr 530 | Trp | Thr | Gly | Asp | Asn 535 | Ala | Ala | Thr | Trp | Gly 540 | Asp | Leu | Arg | Tyr |
| Ser 545 | Ile | Asn | Thr | Met | Leu 550 | Ser | Phe | Gly | Leu | Phe 555 | Gly | Met | Pro | Met | Ile 560 |
| Gly | Ala | Asp | Ile | Cys 565 | Gly | Phe | Asn | Gly | Asn 570 | Thr | Thr | Glu | Glu | Leu 575 | Cys |
| Gly | Arg | Trp | Ile 580 | Gln | Leu | Gly | Ala | Phe 585 | Tyr | Pro | Phe | Ser | Arg 590 | Asp | His |
| Ser | Ala | Ile 595 | Phe | Thr | Val | Arg | Arg 600 | Glu | Leu | Tyr | Leu | Trp 605 | Pro | Ser | Val |
| Ala | Ala 610 | Ser | Gly | Arg | Lys | Ala 615 | Leu | Gly | Leu | Arg | Tyr 620 | Gln | Leu | Leu | Pro |
| Tyr 625 | Phe | Tyr | Thr | Leu | Met 630 | Tyr | Glu | Ala | His | Met 635 | Thr | Gly | Ala | Pro | Ile 640 |

```
Ala  Arg  Pro  Leu  Phe  Phe  Ser  Tyr  Pro  His  Asp  Val  Ala  Thr  Tyr  Gly
               645            650                           655

Val  Asp  Arg  Gln  Phe  Leu  Leu  Gly  Arg  Gly  Val  Leu  Val  Ser  Pro  Val
               660            665                           670

Leu  Glu  Pro  Gly  Pro  Thr  Thr  Val  Asp  Ala  Tyr  Phe  Pro  Ala  Gly  Arg
               675            680                           685

Trp  Tyr  Arg  Leu  Tyr  Asp  Tyr  Ser  Leu  Ala  Val  Ala  Thr  Arg  Thr  Gly
     690                 695                      700

Lys  His  Val  Arg  Leu  Pro  Ala  Pro  Ala  Asp  Thr  Val  Asn  Val  His  Leu
705                      710                 715                           720

Thr  Gly  Gly  Thr  Ile  Leu  Pro  Leu  Gln  Gln  Ser  Ala  Leu  Thr  Thr  Ser
               725                      730                           735

Arg  Ala  Arg  Arg  Thr  Ala  Phe  His  Leu  Leu  Val  Ala  Leu  Ala  Glu  Asp
               740                 745                      750

Gly  Thr  Ala  Ser  Gly  Tyr  Leu  Phe  Leu  Asp  Asp  Gly  Asp  Ser  Pro  Glu
          755                      760                 765

Tyr  Gly  Arg  Arg  Ser  Asp  Trp  Ser  Met  Val  Arg  Phe  Asn  Tyr  Lys  Ile
     770                 775                      780

Pro  Asn  Asn  Lys  Gly  Ala  Ile  Lys  Val  Lys  Ser  Glu  Val  Val  His  Asn
785                      790                 795                           800

Ser  Tyr  Ala  Gln  Ser  Arg  Thr  Leu  Val  Ile  Ser  Lys  Val  Val  Leu  Met
               805                      810                           815

Gly  His  Arg  Ser  Pro  Ala  Ala  Pro  Lys  Lys  Leu  Thr  Val  His  Val  Asn
               820                 825                      830

Ser  Ala  Glu  Val  Glu  Ala  Ser  Ser  Ala  Gly  Thr  Arg  Tyr  Gln  Asn
          835                 840                 845

Ala  Gly  Gly  Leu  Gly  Gly  Val  Ala  His  Ile  Gly  Gly  Leu  Ser  Leu  Val
     850                      855                 860

Val  Gly  Glu  Glu  Phe  Glu  Leu  Lys  Val  Ala  Met  Ser  Tyr
865                 870                 875
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide     ( v ) FRAGMENT TYPE: internal     ( v i ) ORIGINAL SOURCE:
        ( A ) ORGANISM: Arabidopsis thaliana     ( v i i ) IMMEDIATE SOURCE:
        ( B ) CLONE: EST 38A2T7

( x i ) SEQUENCE DESCRIPTION: SEQ ID NO:5:

```
Trp  Ile  Asp  Met  Asn  Glu
 1                     5
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide (v) FRAGMENT TYPE: internal (vi) ORIGINAL SOURCE:
   (A) ORGANISM: Arabidopsis thaliana (vii) IMMEDIATE SOURCE:
   (B) CLONE: EST 38A2T7

(xi) SEQUENCE DESCRIPTION: SEQ ID NO:6:

Gly Glu Val Trp Pro Gly
1               5

(2) INFORMATION FOR SEQ ID NO:7:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (v) FRAGMENT TYPE: internal (xi) SEQUENCE DESCRIPTION: SEQ ID NO:7:

Asp Gly Trp Ile Asp Met Asn Glu
1               5

CLONED α-GLUCOSIDASE FROM BARLEY

This invention was made with United States government support awarded by the United States Department of Agriculture (USDA). USDA-CRIS project numbers: 3655-21440-001 and 3655-21410-001. The U.S. government has certain rights in this invention.

FIELD OF THE INVENTION

The present invention relates to a full-length cloned cDNA which encodes an alpha-glucosidase enzyme from barley.

BACKGROUND OF THE INVENTION

Alpha-amylase (EC 3.2.1.1) was once believed to be the only enzyme involved in the initial attachment to and degradation of starch granules in germinating cereal seeds. This enzyme is synthesized de novo in the aleurone (outer seed layer) and scutellum in response to gibberellic acid-GA$_3$ (GA) and is secreted into the endosperm. The other amylolytic enzymes (β-amylase [EC 3.2.1.2], limit dextranase [debranching enzyme, EC 3.2.1.41], and α-glucosidase [EC 3.2.1.20]) were believed not to be involved in the attachment and degradation of the granule, but rather, were believed to serve only to efficiently hydrolyze the maltodextrins released by β-amylase. Alpha-amylase endolytically and β-amylase exolytically hydrolyze the α-1,4-D-glucosidic linkages in amylose and amylopectin, producing maltose. Alpha-glucosidase exolytically hydrolyzes the α-1, 4-, α-1,6-, α-1,3- and α-1,2-D-glucosidic bonds in starch derived glucans and releases glucose. The glucose is then metabolized, presumably in the scutellum.

As long ago as the late 1930's, researchers postulated the involvement of additional factors required for the efficient breakdown of native starch granules. Recent evidence suggests that α-glucosidase can bind to starch granules and accelerate their initial hydrolysis in the presence of α-amylase (Sun, et al. Arch Biochem Biophys 284: 298–305, 1991; Sun, et al. Plant Physiol 94: 320–327, 1990). In vitro, barley α-glucosidase can hydrolyse native starch granules at rates comparable to α-amylase. An up to ten-fold synergism in starch grain hydrolysis was observed when α-glucosidase was used with α-amylase. It is believed this synergism is partly due to α-glucosidase's ability to hydrolyze glucosidic bonds other than α-1,4- and α-1,6- that are present on the surface of the granule. These sites could potentially act as barriers to hydrolysis by α-amylase. Some of this synergism can also be attributed to the removal of maltose, which can inhibit α-amylase activity when present at high concentrations. In independent work, the antihyperglycemic drug Bay m 1099 (a sugar analogue) was shown to inhibit α-glucosidase activity in germinating wheat seeds (Konishi, et al., Biosci Biotech Biochem 58: 135–139, 1994). The researchers noted a 48% decrease in the initial rate of starch degradation as well as a reduction in glucose levels.

A number of researchers have studied various aspects of barley α-glucosidase activity over the past thirty years. Barley α-glucosidase activity is present during early seed development with levels decreasing during maturation. Low amounts are present in the aleurone, pericarp, and embryo of ungerminated grain. After germination, a six-fold increase in activity is seen. This new activity is found in the scutellum, aleurone, endosperm and embryo. Levels are enhanced by GA. This increase is the result of de novo synthesis and occurs just before the synthesis of α-amylase and limit-dextranase. Two α-glucosidase and two maltase isoforms have been identified in germinated barley. Two other α-glucosidase charge forms, high- and low-isoelectric points, have been studied (Sun, et al., Plant Physiol 94: 320–327, 1990). They possess molecular weights (SDS-PAGE) of 65 and 32 kDa, respectively. There are significant differences in their affinities towards various disaccharides and starch substrates.

To date, there are no published reports describing the cloning and characterization of α-glucosidase genes from plant sources. Other α-glucosidase genes, and genes for other enzymes with α-1,4- and/or α-1,6-exoglucolytic activity, have been cloned in bacteria, fungi, insects and mammals. These enzymes have a $(\beta/\alpha)_8$ structure and fall into one of three glycosyl hydrolase families based on function and amino acid homology (Svensson, FEBS Let 230: 72–76, 1988). These families include α-amylase-related maltases (family 13), fungal glucoamylases (family 15) and α-glucosidases (family 31). There are significant differences in physical properties and substrate specificities both within and between the families. These enzymes evolved and are specialized with respect to the organism, cell type, and their environment. Of these enzymes, the α-glucosidase from barley seed is the most appropriate in hydrolyzing starch in cereals.

Alpha-amylase is one of the most widely used industrial enzymes, being vital for starch hydrolysis in many processes including brewing, syrup production, and textile manufacturing. α-amylases are usually combined with various bacterial or fungal glucoamylases as their combined action most efficiently liquefies and saccharifies starches.

To date, no plant α-glucosidase has been used to replace or supplement glucoamylase in industrial starch hydrolysis systems. The cloning, characterization and optimization by reengineering of α-glucosidase could provide a valuable new enzyme for industrial purposes, as well as novel enzyme with new specificities. In addition, useful DNA sequence characteristics can be identified, which can be used as hybridization probes for identifying germplasm with high levels of efficient hydrolytic enzymes.

SUMMARY OF THE INVENTION

In one embodiment, this invention provides a biologically pure sample of DNA which DNA comprises a sequence encoding the expression of barley α-glucosidase.

In other aspects, the invention provides a vector and microbial host containing a DNA sequence sufficiently homologous to SEQ ID NO:3 so as to code for the expression of barley α-glucosidase, and a DNA construct comprising a DNA sequence sufficiently homologous to SEQ ID NO:3 so as to code for the expression of barley α-glucosidase, together with a promoter located 5' to the DNA coding sequence and a 3' termination sequence.

In another embodiment, the invention provides a method of preparing barley α-glucosidase by culturing, under conditions suitable for the expression of barley α-glucosidase, a microbial host transformed by a vector containing a DNA sequence sufficiently homologous to SEQ ID NO:3 so as to code for the expression of barley α-glucosidase, and recovering the barley α-glucosidase from the culture.

It is an object of the present invention to provide a cloned gene which encodes the enzyme barley α-glucosidase.

It is also an object of the present invention to provide a method for the preparation of the enzyme barley α-glucosidase, an enzyme which, when used with the enzyme α-amylase, increases the rate of starch grain hydrolysis by ten-fold.

Other features and advantages of the invention will be apparent from the following description of the preferred embodiments thereof and from the claims.

BRIEF DESCRIPTION OF THE DRAWINGS

FIGS. 2A–2C illustrates conservation between the deduced amino acid sequence of barley α-glucosidase clone pAGL.2737 and other α-glucosidases. Human lysosomal α-glucosidase (1), rabbit isomaltase (2), rabbit sucrase (3), *Schwanniomiyces occidentalis* glucoamylase (4), *Candida tsukubaensis* α-glucosidase (5), and barley α-glucosidase (6). Barley amino acids which are identical to all or the majority of the sequences are indicated by capital and small case letters above the aligned sequences, respectively. The catalytic region is underlined. The catalytic Trp (W) and Asp (D) residues are indicated (*).

DETAILED DESCRIPTION OF THE INVENTION

The present specification describes the isolation of an α-glucosidase cDNA clone (pAGL.2737, SEQ ID NO:3) from barley aleurone tissue. The deduced amino acid sequence of the α-glucosidase polypeptide was compared to the well characterized α-glucosidase and amylolytic enzymes from other organisms. The level of α-glucosidase mRNA and enzyme activity were analyzed in germinating seed tissues and the influence GA has on them in isolated aleurones.

The present specification describes a biologically pure sample of DNA including a DNA sequence coding for the expression of barley α-glucosidase. One particular α-glucosidase sequence is set forth as SEQ ID NO:3. The present specification also includes a vector and microbial host comprising a DNA sequence containing either SEQ ID NO:3 or a portion or version of SEQ ID NO:3 sufficient to effect coding for the expression of barley α-glucosidase, and also a gene construct containing either SEQ ID NO:3 or a portion or version of SEQ ID NO:3 sufficient to effect coding for the expression of barley α-glucosidase, together with a promoter located 5' to the DNA coding sequence and a 3' termination sequence.

Gene Construct

To express a barley α-glucosidase gene sequence in a host, it is required that the DNA sequence containing the α-glucosidase coding sequence, such as SEQ ID NO:3 or a version of SEQ ID NO:3 sufficient to effect coding for the expression of barley α-glucosidase, be combined with a promoter located 5' to the DNA coding sequence and a 3' termination sequence. Commonly used methods of molecular biology well-known to those of skill in the art may be used to manipulate the DNA sequences.

By "gene construct" we mean any of a variety of ways of combining the protein-encoding sequence with promoter and termination sequences in a manner that operably connects the promoter and termination sequences with the protein-encoding sequence. Typically, the promoter sequence will be 5' or "upstream" of the protein-encoding sequence, while the termination sequence will be 3' or "downstream" of the protein-encoding sequence.

For example, these two sequences may be combined together on a plasmid or viral vector, and inserted into a microbial host. Other functional sequences, such as secretion signals, polyadenylation and termination sequences, may be added to the gene construct. Alternatively, the protein-encoding, promoter, and termination sequences may be combined together with only other needed functional sequences and used without a vector.

SEQ ID NO:3 and Variants

SEQ ID NO:3, and the method used to obtain it, is described below. The Examples below disclose that SEQ ID NO:3 is sufficient to effect coding for the expression of barley α-glucosidase. However, we envision that the full-length coding region of SEQ ID NO:3 could possibly be truncated from either end, and still encode an active enzyme. One skilled in the art of molecular biology would be able to take SEQ ID NO:3 and perform truncation and deletional analysis experiments to determine what portion of SEQ ID NO:3 is essential to effect coding for the expression of barley α-glucosidase. One could create a genetic construct with the candidate deletion mutations and perform experiments as described below in the Examples, to test whether such deletion mutation sequences effect coding for the expression of barley α-glucosidase. Expression of barley α-glucosidase activity indicates a successful deletion mutant. In this manner, one could determine which parts of SEQ ID NO:3 are essential for expression of barley α-glucosidase.

One skilled in the art of molecular biology would appreciate that minor deletions, additions and mutations may not change the attributes of SEQ ID NO:3. Many of the nucleotides of SEQ ID NO:3 are probably not essential for its unique function. To determine whether or not an altered sequence has sufficient homology with SEQ ID NO:3 to function identically, one would simply create the candidate mutation, deletion or alteration and create a gene construct including the altered sequence together with promoter and termination sequences. This gene construct could be tested as described below in the examples for the occurrence of barley α-glucosidase.

It is very well known, for example, that the genetic code is degenerate, meaning that more than one codon, or set of three nucleotides, codes for each amino acid. Thus it is possible to alter the DNA coding sequence to a protein, such as the barley α-glucosidase described here, without altering the sequence of the protein produced. Selection of codon usage may affect expression level in a particular host. Such changes in codon usage are also contemplated here.

EXAMPLES

Seeding preparation

Barley (*Hordeum vulgare* L. cv Morex) seeds 1987 crop year, were supplied by Darrell Wesenberg, USDA Agricultural Research Service, Small Grains Germplasm Research Facility, Aberdeen, Id. Seeds were sterilized for 10 min in 1% w/v hypochlorite and then rinsed extensively in deionized water. Seeds were imbibed for 8 hours in 2 mM $CaCl_2$ and then spread on damp Kimpack germination paper. Seedlings were grown up to 10 days at 16° C. in complete darkness. After removing the shoots and roots, kernels were weighed, frozen in liquid nitrogen, and stored at −70° C. until used.

Other tissues were prepared for RNA isolation. Embryos and scutula were dissected from seeds germinated for 3 days at 16° C. Roots and shoots were harvested from seeds germinated for 7 days. Hypocotyls and coleoptiles were harvested from plants grown in soil without light for 6 days at 16° C. This same lot was grown for an additional 3 days under a 12 hour light/12 hour dark cycle for collection of primary leaves. Whole developing seeds were harvested 4 to 20 days post anthesis and pooled. Wheat kernels (*Tricicum aestivum* L. cv Chinese Spring) were obtained from seeds germinated for 7 days.

Aleurone treatment

Embryos were excised and discarded from dry Morex seeds. De-embryonated half-seeds were sterilized then distributed onto Kimpacks dampened with 2 mM $CaCl_2$. After 5 days, aleurones were removed and incubated in a Na succinate/$CaCl_2$ buffered solution (Belanger, et al., Plant Physiol 83: 1354–1358, 1986) with the addition of penicillin and gentamicin (Skadsen, Plant Physiol 102: 195–203, 1993). GA was added to a final concentration of 1 µM ($GA_3$, Sigma). After 24 hours of incubation, the aleurones were rinsed in fresh buffer, blotted, weighed, and stored at –70° C.

Enzyme assays

Germinated seeds were ground using a mortar and pestle. One gram (fresh weight) of kernels was extracted in 10 ml of buffer A (50 mM $Na_2CO_3$/$NaHCO_3$ pH 9, 1M NaCl, 1% Triton X-100, 2 mM β-mercaptoethanol) or buffer B (200 mM Na acetate pH 5.5, 10 mM $CaCl_2$). The homogenates were centrifuged at 10,000 rpm for 20 min at 4° C. in a JA-20 rotor. The supernatant was collected and dialyzed against 10 mM Na succinate pH 4.2 for 18 hours at 4° C.

Alpha-glucosidase activity was determined as described in Sun, et al., Plant Physiol 94: 320–327, 1990, with modifications. Up to 100 µl of sample extracted with buffer A was incubated with 1 ml of 1 mg/ml p-nitrophenyl α-D-glucopyranoside (PNPG) (Sigma) in 50 mM Na succinate buffer, pH 4.2. After incubating for 30 min at 37° C., 100 µl of 2M Na bicarbonate was added to terminate the reaction and allow color development. The amount of p-nitrophenyl released was measured at 420 nm. Activity is expressed as the number of nmoles of PNP released from substrate per minute per gram fresh weight (gfw) of tissue.

Total α-amylase activity was measured in samples extracted with buffer B. Samples were heated to 70° C. for 20 min and microfuged. Supernatants were combined with soluble starch (Lintner potato starch, Sigma) and incubated at 30° C. for 10 to 30 min. Reducing sugars were measured. After boiling, the reactions were cooled to 22° C. then clarified by microfuging. The absorbance at 547 nm was measured, and activity was determined relative to a maltose standard. Activity is expressed as µmoles of maltose equivalents produced per minute per gfw.

Construction of cDNA libraries

A total seedling cDNA library, contained in the Eco RI site of λZapII (Stratagene), was prepared from polysomal poly(A)⁺RNA isolated from 3- and 4-day-old malted seedlings of Morex (Skadsen, et al., J. Cereal Sci 19: 199–208, 1994). A GA-treated aleurone cDNA library was prepared from poly(A) ⁺RNA purified from isolated aleurones treated with GA for 30 hours. cDNA synthesis and directional insertion were achieved by reverse transcription using a $T_{15}$-NotI primer-adaptor and ligation into λgt11 arms containing Eco RI and Not I sites, performed as described in the technical manual (Promega).

cDNA cloning

The cDNA libraries were hybridized with heterologous DNA probes from α-glucosidase, and similar enzymes, in other systems. Their glycosyl hydrolase family number, name, and contributor are noted. Family 13: maltase from *Saccharomyces Cerevisiae* (Bei Yao, Albert Einstein College of Medicine) (Hong, et al., Gene 41: 75–84, 1986) and mosquito (Anthony James, University of California-Irvine) (James, et al., Gene 75: 73–83, 1989). Family 15: glucoamylase from *Aspergillus oryzae* (Katsuhiko Kitamota, National Research Institute of Brewing) (Hata, et al., Gene 108: 145–150, 1991) and *Saccharomycopsis fibuligera* (Eva Hostinova, Slovak Academy of Science) (Hostinova, et al., FEMS Microbiol Lett. 83: 103–108). Family 31: α-glucosidase from human lysosome (Frank Martiniuk, New York University Medical Center; Arnold JJ Reuser, Erasmus University Rotterdam) (Hoefsloot, et al., EMBO J 7: 1697–1704, 1988); Martiniuk, et al., DNA Cell Biol 9: 85–94, 1990) and Arabidopsis EST cDNA clone 38A2T7- possessing homology with human lysosomal α-glucosidase (Keith Davis, Ohio State University, unpublished; GenBank accession t04333), sucrase-isomaltose complex from human (Dallas Swallow, University College London) (Chantret, et al., Biochem J 285: 915–923, 1992; Green, et al., Gene 57: 101–110, 1987), and rabbit intestine (Ned Mantei, Swiss Federal Institute of Technology Zurich) (Hunziker, et al., Cell 46: 227–234, 1986).

Phage from the malted seedling and GA-treated aleurone cDNA libraries were incubated with *E. coli* XL-1 Blue and LE392 cells, respectively, and plated. Plaques were transferred onto nitrocellulose (Schleicher and Schull) (Benton, et al., Science 196: 180–182, 1977). Probes were radiolabeled using a random hexamer-primed Klenow reaction (Feinberg, et al., Anal Biochem 132: 6–13, 1983) and [α-$^{32}$P]dCTP (3000 Ci/mmol, DuPont). The probes were added to an SSC-buffered hybridization solution (Thomas, Meth Enzymol 100: 255–266, 1983) containing 10% w/v dextran sulfate, as performed previously according to Skadsen, et al. Hybridization and rinses were performed under low stringency conditions. The filters were placed in x-ray cassettes with XAR-5 film (Kodak) for up to 5 days.

Another set of filters was hybridized with oligonucleotide probes. Several degenerate oligonucleotides—specific to the catalytic, substrate-binding, and other conserved sites of these enzymes (Svensson, FEBS Let 230: 72–76, 1988) were synthesized. The oligos were 5'-end labeled with [λ-$^{32}$P]ATP (DuPont) and polynucleotide kinase (Promega). Hybridization and rinsing were performed at 37° C. (Sambrook, et al., *Molecular Cloning: A Laboratory Manual*, Ed 2, pp 1.42–1.46, 9.38–9.40, 1989).

Oligonucleotide Probe

α-Glucosidases and enzymes with similar activity fall into one of three families. The catalytic and substrate binding sites of a single family are highly conserved in a variety of organisms. These sites have been diagrammed. Several degenerate oligonucleotides, specific to the DNA encoding these sites, were synthesized. Oligos AGLUC3 and 6 represent the substrate binding regions of α-amylase related maltases. These oligos were converted to radiolabeled probes and hybridized to the libraries. Several positive plaques were detected. Unfortunately, the cDNA clones later proved to be α-amylase high-pI clones.

A third oligo, AGLUC4Y, was constructed. This oligo represents the catalytic region of maltase and was predicted to be more specific for maltase and less for α-amylase. A fourth oligo, AGLUC4HR, was also constructed. This oligo represents the catalytic site of α-glucosidases in family 31. Hybridization of the libraries with these oligos failed to detected positive clones in the library.

Heterologous Gene Probes

The libraries were hybridized with α-glucosidase genes from other organisms. Members of each of the three glycosyl hydrolase families were represented. Hybridization with probes constructed from full-length genes allows a potentially greater number of sites on the cDNA to be targeted. These clones and the source from which they were received are described. (*Family* 31): human lysosomal α-glucosidase (Martiniuk et al, Matiniuk; Hoefsloot et al, Reuser), human intestinal pro-sucrase-isomaltase complex (Green et al, Chantret et al, Swallow), and rabbit intestinal pSI (Hunziker et al, Mantei); (Family 13): yeast maltase (Hong and Marmur, Yao and mosquito maltase (James et al, James); (Family 15) Aspergillus glucoamylase (Hata et al, 1991, Kitamoto 7-16-92) and Saccharomycopsis fibuligera glucoamylase (Hostinova et al, Hostinova). However, hybridization with representatives from the three families failed to detect positive plaques.

Antibody Screening

A rabbit anti-α-glucosidase antibody was prepared from commercially available rice α-glucosidase by a collaborator (Dr. J. J. Santer). The antibody cross reacts with maltase from poplar. The cDNA libraries were plated and induced to express their fusion protein. The protein was transferred to nitrocellulose and then screened with the antibody. Positive plaques were not detected. The antibody was extensively studied against α-glucosidase in barley seed extracts. These results were not satisfactory.

Arabidopsis EST Gene Probe

The cDNA libraries were hybridized with a probe constructed from Arabidopsis EST 38A2T7 cDNA which possesses an open reading frame that is homologous to human lysosomal α-glucosidase. This sequence (400 bases) was released to Genbank, Accession NO. T04333. Analysis of the 400 base sequence detected an "α-glucosidase-like" catalytic site (WIDMNE) 230 bases in from the 5' end. An additional conserved site (GEVWPG) was located 132 bases upstream. A frame shift and premature termination were also detected, which were attributed to an error in sequencing. We also concluded that this was a partial-length clone that was probably 1900 bp short of the true 5' end, if it were to be the same length as the 3600 bp human cDNA. We requested and received this clone from Keith Davis, Ohio State University. We discovered the insert size was 1700 bp. The insert was converted to a probe and hybridized to the libraries as well as northern blots. Neither produced a signal.

PCR Amplification of Degenerate Primers

Figure 2B:
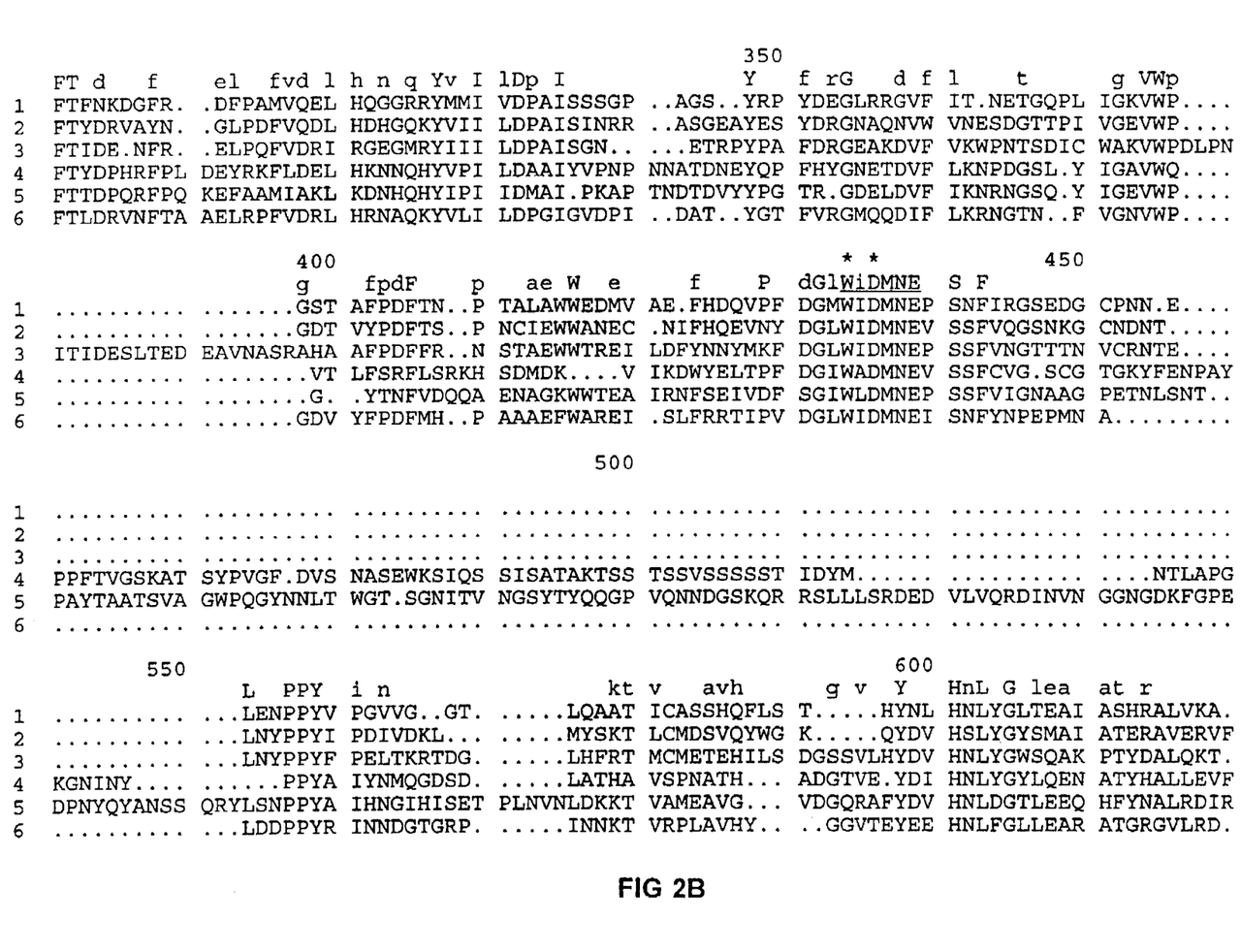

A degenerate 18-base oligonucleotide (5'-YTCRTTCATRTCDATCCA-3', "4HR-AS") (SEQ ID NO:1) was synthesized. This oligo is complementary to the conserved catalytic region (WIDMNE), see FIG. 2B) of family 31 members: human lysosomal α-glucosidase (Hermans, et al., J. Biol Chem 266: 13507–13512, 1991), human and rabbit (Chantret, et al., Biochem J 285: 915–923, 1992; Hunziker, et al., Cell 46: 227–234, 1986) intestinal sucrase-isomaltase complex, Candida tsukubaensis α-glucosidase (Kinsella, et al., Eur J Biochem 202: 657–664, 1991), and Schwanniomyces occidentalis glucoamylase (Dohman, et al., Gene 95: 111–121, 1990). A second degenerate 17-base oligonucleotide (5'-GGNGARGTNTGGCCNGG-3', "MalG-S") (SEQ ID NO: 2) was also synthesized. This sequence encodes the conserved region (GEVWPG) and is located 44 aa/132 nt upstream from the catalytic region.

These two oligos were used as primers to amplify by PCR the predicted 132 bp product, using cDNA as a template. One ng of total cDNA derived from GA-treated aleurones was combined with 400 ng of each oligo. This was assembled in a final 100 μl reaction containing PCR buffer with 4 mM MgCl$_2$ and 200 μM dNTPs. Reactions were overlaid with 60 μl of mineral oil and "hot-started" at 70° C. prior to adding 2.5 u of AmpliTaq DNA polymerase (Perkin-Elmer). Amplification was carried out with 35 cycles of denaturation at 95° C. for 1 min, annealing at 36° C. for 2 min, and extension at 72° C. for 2 min. This was followed by incubation at 72° C. for 7 min.

Fifteen μl of the reaction product was electrophoresed on a 56 polyacrylamide-Tris borate (TBE) gel. The gel was stained with ethidium bromide then analyzed. A 132 bp product was excised from the gel, ground in TE and resuspended overnight at 4° C.

The 132 bp product was re-amplified, electrophoresed on a 1.2% low-melting agarose-TBE gel, excised, and purified using agarose (Boehringer Mannheim). The 132 bp DNA was converted to a radiolabeled probe in a Klenow reaction containing 100 ng of DNA and 100 ng of each specific primer (in lieu of random hexamers). The two libraries were then hybridized with the probe at 46° C. Filters were washed four times in 2× SSC/0.1% SDS at 22° C. for 15 min each and then four times in 0.2× SSC/0.1% SDS at 46° C. for 15 min each. Positive plaques were purified. The λZapII candidates were in vivo-excised with R408 helper phage using the procedure outlined in the applications guide (Stratagene). λgt 11 candidates were amplified in liquid culture and pelleted with LambdaSorb Phage Adsorbent (Promega) using the procedure described in the applications guide. cDNA inserts in λgt 11 were removed by cutting with Eco RI and NotI and separated on a 1% SeaPlaque agarose (Marine Colloids) gel. Insert DNA was subcloned into the Eco RI and NotI sites of pBluescript SK-(Stratagene).

Sequence analysis

All clones were restriction cut and electrophoresed on 1% agarose gels to determine the lengths. DNA was Southern blotted onto nitrocellulose (Sambrook, et al., Molecular Cloning: A Laboratory Manual, Ed 2, pp. 1.42–1.46, 9.38–9.40, 1989) and hybridized with the 132 bp probed, as above. pAGL.2737, the full-length clone (SEQ ID NO: 3), and subclones were sequenced by the dideoxy chain-termination method (Sanger, et al., Proc Natl Acad Sci USA 74: 5463–5467, 1977) using Sequenase (US Biochemical Corp). The DNA sequence information was analyzed using the Genetics Computer Group Sequence Analysis Software Wisconsin Package.

An amino acid sequence alignment between barley and the other α-glucosidases, belonging to glycosyl hydrolase family 31, was performed. The names, polypeptide lengths, regions analyzed and size, and SwissProt accession numbers were as follows: human lysosomal α-glucosidase (952 aa) (189–862 [674 aa]) P10253 (Hoefsloot, et al., EMBO J 7 1697–1704, 1988); rabbit intestinal pro-sucrase-isomaltose complex (1827 aa) 168–835 [668 aa] isomaltose, 1040–1729 [690 aa] sucrase) P07768 (Hunziker, et al., Cell 46: 227–234, 1986); Schwanniomyces occidentalis glucoamylase (958 aa) (130–871 [742 aa]) P22861 (Dohmen, et al., Gene 95: 111–121, 1990); Candida tsukunbaensis α-glucosidase (1070 aa) (122–975 [855 aa]) P29064 (Kinsella, et al., Eur J Biochem 202: 657–664, 1991).

RNA Isolation and Northern Blot Analysis

RNA was purified from caryopses of 2- to 7-day-old seedlings, isolated aleurones and the miscellaneous tissues as described in Skadsen, Plant Physiol 102: 195–203, 1993. Aurintricarboxylic acid was omitted when the RNA was intended for cDNA synthesis. Ten μg of total RNA from each sample was electrophoresed on 1.2% agarose-formaldehyde gels. One ng of a NaOH-denatured insert DNA (a partial-length α-glucosidase cDNA clone 2150 bp in length) served as a standard. Gels were stained with ethidium bromide, photographed, and then blotted onto nitrocellulose (Rave, et al., Nucl Acids Res 6: 3559–3567, 1979). The blots were hybridized with a probe prepared from the 2150 bp clone insert. Hybridization was conducted at 62.5° C. for 16 hours. Washings were as above but with the final set in 0.1× SSC/0.1% SDS at 62.5° C. Filters were exposed to film for two or three time periods so as not to exceed the linear response range of the film. Duplicate blots were screened with a previously cloned barley actin probe. Blots were also screened with probes constructed from either the high-pI α-amylase cDNA (clone pM/C) (Rogers, J Biol Chem 258: 8169–8174, 1983); or the low-pi cDNA (clone E) (Rogers, et al., J Biol Chem 258: 8169–8174, 1983).

Genomic DNA isolation and Southern blot analysis

Genomic DNA was prepared from etiolated shoots in the presence of ethidium bromide followed by ultracentrifugation in CsCl (Kislev, et a., Plant Physiol 66: 1140–1143, 1980; Sambrook, et al., Molecular Cloning: A Laboratory Manual, Ed. 2, pp. 1.42–1.46, 9.38–9.40, 1989). Seven µg of DNA was digested with XbaI, SspI, PvuII, or PstI restriction enzymes and electrophoresed on a 0.7% agarose Tris-acetate gel. Lambda phage DNA digested with HindII or PstI served as molecular size markers. The gel was Southern blotted onto a Nytran nylon membrane (Schleicher and Schuell). The filter was baked and then prehybridized as before (Skadsen, Plant Physiol 102: 195–203, 1993) in an SSPE-buffered solution (Thomas, Meth Enzymol 100: 255–266, 1983). The blot was hybridized with a probe prepared from the insert of a near full-length 2600 bp α-glucosidase cDNA clone, pAGL.2600. Hybridization was carried out at 65° C. for 16 hours. Washings were as before with the final set of rinses in 0.1× SSPE/0.1% SDS at 65° C.

RESULTS

Changes in enzyme activity during germination

Figure 1:
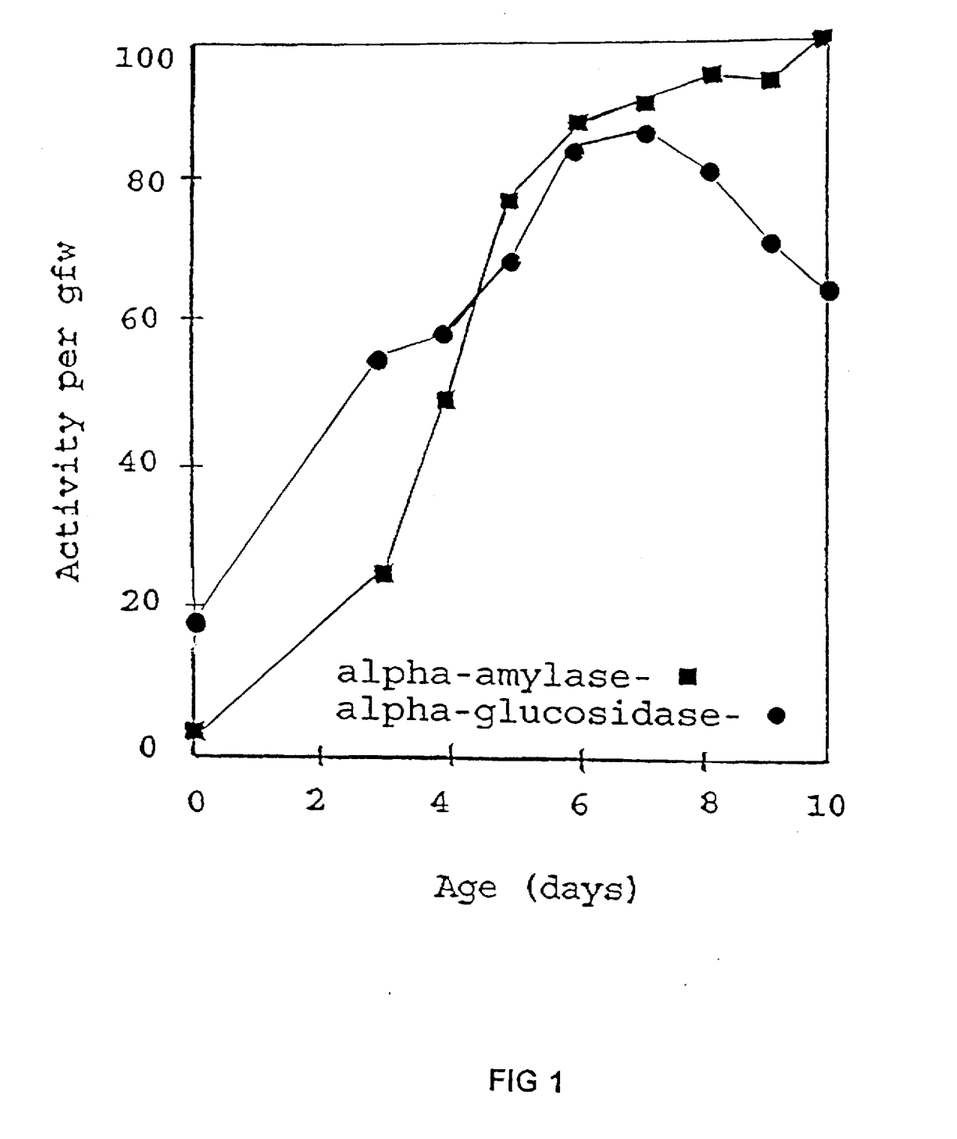
FIG. 1 is a graph illustrating temporal changes in α-amylase enzyme activities in germinating seeds. Days represent days post onset of imbibition. Units of activity represent nmol p-nitrophenol liberated/min/gfw×10 and μmol maltose equivalents/min/gfw×40, respectively.

Both α-glucosidase and α-amylase activities increase during germination. As can be seen by referring to FIG. 1, α-glucosidase activity was present at low levels in the unimbibed seed (day 0). Activity steadily increased through day 7, reaching levels five-fold greater than day 0, and then declined. Alpha-amylase activity was essentially nonexistent at day 0. Activity increased in concert with α-glucosidase and continued to increase slowly after day 7.

Isolation of the cDNA clone

Cloning was unsuccessful when heterologous probes and degenerate oligonucleotides were used to screen the cDNA libraries. The failure of success of these strategies was due to insufficient homology to previously isolated α-glucosidase genes.

Success in cloning came via PCR. PCR amplification, using degenerate primers designed after members of family 31 and GA-treated aleurone cDNA as template, generated a product with a predicted 132 bp size (gel not shown). Hybridization of the libraries with a probe constructed from the 132 bp product detected plaques in both (autoradiograms not shown). A full-length 2737 bp cDNA, pAGL.2737, SEQ ID NO: 3, which appears (from Southern blotting) to be present in a single form, was identified and characterized by restriction analysis and DNA sequencing techniques.

Amino acid sequence analysis

The barley α-glucosidase cDNA clone encodes a polypeptide that is highly homologous to human lysosomal α-glucosidase. Five cDNA clones of varying length were initially selected for preliminary sequencing and translation of the three forward reading frames. The deduced amino acid sequence from a non-full-length 1650 bp clone, isolated from the malted seedling library, identified a 9 amino acid region, DGLWIDMNE (Asp Gly Leu Trp Ile Asp Met Asn Glu), approximately 150 bases downstream from its 5' end (position 432 on FIGS. 2A–2C). This region is identical to the catalytic region of human lysosomal α-glucosidase and other members of family 31. As can be seen by referring to FIGS. 2A–2C, subsequent sequencing and translation of the entire pAGL.2737 clone (SEQ ID NO:3; the translated barley α-glucosidase sequence is presented as SEQ ID NO:4) revealed additional and high overall homology with human lysosomal α-glucosidase, rabbit intestinal isomaltose and sucrase, Schwanniomyces occidentalis glucoamylase, and Candida tsukubaensis α-glucosidase. When barley is compared with each of the above individually (figure not shown), the percent amino acid identities and similarities are 43/64, 45/66, 41/61, and 39/59, respectively.

Analysis of Northern Blots

Alpha-glucosidase mRNA levels increase during germination. Northern blots were used to study temporal changes in α-glucosidase mRNA levels in germinating seeds. The northern blots were hybridized with barley α-glucosidase, low-pI α-amylase, high-pI α-amylase, or actin probes. One ng of a partial-length (2150 bp) barley α-glucosidase cDNA served as a hybridization control when the northern blot was hybridized with barley α-glucosidase.

A northern blot containing total RNA from seeds germinated for 2 to 7 days detected the presence of a 2737-base mRNA after hybridization with a probe constructed from the α-glucosidase cDNA. Low levels were present in the 2nd day sample. The level increased several-fold more by day 3, peaked, and then plateued before decreasing slightly between days 5 and 7. The expression pattern of α-glucosidase mRNA was compared with the two forms of α-amylase mRNA, on duplicate blots. Low-pI α-amylase mRNA was barely detectable at day 2, increased and peaked at day 5, then declined by day 7. High-pI α-amylase mRNA reached a high and near maximal level after day 2, peaked at day 3 or 4, plateaued through day 5, then declined between day 5 and 7. The levels of high-pI message were greater than the low-pI. Hybridization with a probe constructed from actin cDNA represented expression at steady state levels. The 1500-base actin mRNA was at low levels at day 2, increases greatly by day 3 and was near constant through day 5 before decreasing slightly by day 7.

In separate work, the frequency of the α-glucosidase mRNA was determined indirectly by hybridizing the cDNA library, constructed from polysome-associated mRNA isolated from 3 and 4 days malted seedlings, with probes derived from full-length cDNAs (autoradiograms not shown). Alpha-glucosidase, high-pI α-amylase, low-pI α-amylase and actin were present at 0.21, 0.79, 0.18, and 0.05%, respectively. Free and membrane-bound polysomes from 1 to 7 day-old germinating seeds were fractionated and the mRNA analyzed on northern blots (Skadsen, unpublished). Hybridizations were carried out with the α-glucosidase, high and low-pI α-amylase, cysteine proteinase, and actin probes. Autoradiograms revealed that α-glucosidase, α-amylase, and proteinase mRNAs were associated with the membrane-bound fraction (autoradiogram not shown). Actin mRNA was associated with both but the majority was on the free-form. This suggests that the 2737-base α-glucosidase mRNA's translation product is a secretory protein.

The level of α-glucosidase mRNA in isolated aleurones is highly dependent on the presence of GA. Northern blots were conducted to study induction of α-glucosidase mRNA synthesis in isolated aleurones in response to GA. Northern blots were hybridized with barley α-glucosidase, low-pI α-amylase, or actin probes. RNA from intact kernels germinated for 5 days were included for comparison. One ng of the 2150 bp cDNA served as a hybridization control when the northern blot was hybridized with barley α-glucosidase. A blot containing total RNA from isolated aleurones incubated with and without GA for 24 hours was analyzed. The blot showed dramatic differences. When GA was omitted, only a low level of the 2737-base mRNA was present. However, when GA was present the mRNA was produced at a several-fold greater level; this level exceeded the levels observed in the 5 day germinated seed standard. Comparisons were made between α-glucosidase and low-pI α-amylase mRNA, using duplicate blots (Skadsen, Plant Physiol 102: 195–203, 1993). Blots hybridized with the low-pI α-amylase probe also contained very low levels of mRNA when GA was omitted and high levels when GA was present. The level of actin mRNA was independent of GA and equal in both treatments. In separate work, hybridization of the cDNA library constructed from GA-treated isolated aleurones revealed that α-glucosidase, high-pI α-amylase, low-pI α-amylase, and actin are present at 6, 7, 5.2, 5.7, and 0.05%, respectively (autoradiograms not shown).

Expression in various tissues

Alpha-glucosidase activities have been reported in a variety of seed and non-seed tissues. Northern blots were used to compare α-glucosidase mRNA in various seed and vegetative tissues, including germinating seed tissue (scutellum, aleurone, embryo, and caryopsis), and coleoptile, leaf, root, shoot, and kernel. Developing seed of barley were also compared to wheat. The northern blots were used to determine whether the mRNA found in the aleurone is the same or similar to ones expressed elsewhere. High levels were found in the scutellum and embryo of germinating seeds under high stringency hybridization conditions. This mRNA was at extremely low levels in developing seeds 4 to 20 days (pooled) post-anthesis. The mRNA was not detected, even under low stringency, in leaves, hypocotyls or coleoptiles of young plantlets nor in the roots and shoots from seeds germinated for 7 days. A northern blot containing total mRNA from 7 day-old germinated seeds of wheat (cv 'Chinese Spring') indicated the presence of a 2737-base mRNA following high stringency hybridization and at levels comparable to 5 days germinated seeds from barley.

Southern blot analysis

Southern blots containing restriction enzyme-digested genomic DNA were studied in order to determine the organization of the α-glucosidase gene, including the gene copy number, and possible existence of related or pseudogenes. The Southern blot was conducted with genomic DNA cut with either XbaI, SspI, PvuII, or PstI, and hybridized with pAGL.2600. XbaI and SspI were chosen because these sites do not exist within the cDNA, and they are insensitive to $C^5$-methylation of CG and CNG sites. Although PstI and PvuII sites exist near the 3' end of the cDNA, they were chosen because the 5' portion could be easily tracked. The most accurate interpretation was with SSpI. Under high stringency hybridization conditions, the majority of signal on the autoradiogram corresponded to a 3.8 kb fragment. This suggests the corresponding gene has a single copy number. Minor bands were seen at 4.7 and 3.2 kb, suggesting the existence of as many as two other, related or pseudogenes.

Discussion

These results identify a barley α-glucosidase cDNA clone, pAGL.2737, SEQ ID NO: 3, that encodes a polypeptide homologous to human lysosomal α-glucosidase and other members of glycosyl hydrolase family 31 (Chantret, et al., Biochem J 285: 915–923, 1992; Kinsella, et al., Eur J Biochem 202: 657–664, 1991; Kreis, et al., Eur J Biochem 169: 517–525, 1987). This suggests the barley enzyme belongs to this family as opposed to family 13 (maltase) or 15 (glucoamylase). The interspecific homology between mammals, yeast and plant suggests that during speciation there was a strong selection pressure to maintain this primary sequence. This more than certainly relates to critical structural and functional domains within the enzyme. The barley enzyme and other members of family 31 have not been as thoroughly characterized as family 13 (α-amylase) (Janse, et al., Curr Genet 24: 400–407, 1993; Jespersen, et al., J. Prot Chem 12: 791–805, 1993) and family 15 (glucoamylase) (Coutinho, et al., Protein Engng 7: 393–400, 1994; Sierks, et al., Protein Engng 6: 75–79, 1993; Tonaka, et al. Agric Biol Chem 50: 965–969, 1986). Conserved or unique amino acid regions and residues may indicate the location of additional starch, substrate binding and other key sites.

Transcription of this α-glucosidase mRNA is from a single gene and is positively regulated by GA in isolated aleurones. However, low levels of the mRNA are produced when exogenous GA is not provided. This pattern and the levels (representing 6% of the total mRNA) are very much like those exhibited by low-pI α-amylase. Like α-amylase, enhanced α-glucosidase activity has also been reported in GA-treated aleurones and the incubation medium. This is presumably as a result of increased synthesis and secretion. An increase in the synthesis of α-glucosidase would be consistent with the increase in the mRNA.

In kernels, both α-glucosidase activity and mRNA levels increase during germination. Transcription of this mRNA occurs in the scutellum and embryo in addition to the aleurone. The presence of the mRNA in these three tissues is also consistent with the increased enzyme activity observed by earlier workers. This mRNA is at apparent very low levels in the developing seed and is not expressed in other seedling tissues. This suggests that expression of this gene is developmental and tissue specific. Although α-glucosidase activities are found in these other tissues the pAGL.2752 mRNA is not. Two additional but less intense bands were present on the Southern blot, so the possible existence of other α-glucosidase mRNAs can be speculated.

There are numerous hydrolases in germinated barley seed tissues. For many of them, their synthesis and/or secretion from the aleurone is enhanced by GA. Several of these GA-regulated genes have been cloned and characterized. High and low-pI α-amylase, (1–3, 1–4)-β-D-glucan endohyrolase, aleurain (a putative cysteine proteinase), and the 30 and 37 kDa cysteine endoproteinases (Koehler, et al., The Plant Cell 2: 769–783, 1990) have been described to date. And of the four amylolytic enzymes (α-amylase, β-amylase, α-glucosidase, and limit-dextranase), only α-amylase (Rogers, J Biol Chem 258: 8169–8174, 1983; Rogers, et al., J Biol Chem 258: 8169–8174, 1983) and β-amylase (Kreis, et al., Eur J Biochen 169: 517–525, 1987) have been cloned and characterized. It now appears that this barley α-glucosidase can be added to these lists. The cDNA and genomic clone, as well as modified constructs, can be used as tools to get a better understanding of starch degradation in the germinating seed. Over-expression and antisense approaches are now possible in transgenic barley. Native and modified forms of the enzyme may also be produced at high levels in a yeast expression system or in any other suitable protein expression system and host. Detailed studies of the enzyme's physical properties would then be possible, as well as offering potential industrial applications.

PROPHETIC EXAMPLES

Yeast Expression Cloning

Hypothetically, full-length clones will be recloned into the yeast expression vector pYES2 (Invitrogen Corp.). This vector contains an extensive multiple cloning region situated between the Gal1 promoter and a translation termination sequence. The Not1 and EcoR1 sites are oriented so that the cDNAs (fitted with EcoR1 and Not1 ends) can be inserted in the sense (5' to 3', coding) orientation. This recombinant will be used to transform *Saccharomyces cerevisae* (Burgers and Percival, 1987). Transformed cells will be plated on selective media. Full-length or near full-length clones have a high likelihood of producing functional enzymes if they are inserted into the vector in the correct translational frame. These chances are also increased by the ability of yeast cells to recognize the glycosylation signals of other eukaryotes. The signals of barley's α-glucosidase will be recognized, producing an active α-glucosidase enzyme. If clones do not produce the cognate protein, the recombinant plasmid will be purified and sequenced at the 5' insertional border to determine whether the reading frame has been disrupted. The reading frame will be restored by limited hydrolysis of the 5' end, or by partially filing in the 5' EcoR1 site with a Klenow fragment reaction.

Positive yeast clones will be cultured in rich YEPM medium (Kopetzki et al., 1989) containing 2% galactose. The medium and lysed cells will be assayed for α-glucosidase activity. It is predicted that yeast, being a eukaryote, will recognize the amino acid sequence which facilitates the enzyme's secretion in barley, hopefully exporting the enzymes into the culture medium. It will initially be necessary to assay both the lysed cells and the medium for α-glucosidase captivity. Medium containing 2% glucose will be used to repress the expression of the endogenous yeast α-glucosidase. Barley α-glucosidase, lacking promoter regulatory sequences, should not be repressed.

Barley-specific expression can be further confirmed by immunological testing and isoelectric focusing activity gels. The polyclonal antibodies raised against barley α-glucosidase should react weakly, if at all, to yeast α-glucosidase and strongly to the barley enzyme. Even if the enzyme in yeast is not post-translationally modified precisely as it is in barley, enough of the amino acid sequence should be recognized to provide an unambiguous confirmation. The functional isozyme pattern of the host α-glucosidase will be determined by IEF and staining for enzyme activity. The IEF pattern of recombinant clones will be assessed in relation to the native barley isozymes. There would be little chance that the yeast and barley α-glucosidases will have the same pIs.

Site-directed mutagenesis of catalytic domain

The active site polypeptide will be identified by inhibitor binding and partial sequencing as previously described. This, along with correlative sequence information from related enzymes, will define at least one catalytic amino acid (probably aspartate) and its neighboring amino acids. These are likely to influence the catalytic properties of the enzyme. For example, in fungal glucoamylase, changing a glu to lys and a ser to his nine and ten amino acids (respectively) from the active site asp causes glucoamylase to behave more like α-amylase (Peter Reilly, Iowa St. Univ. personal communication). We anticipate that two types of alterations in catalysis will occur: 1) quantitative alterations in the rate of maltose hydrolysis, and 2) qualitative alterations in substrate specificity. This and the large number of potential mutants which will be created require that an efficient screening method be employed.

In order to have control over the range of mutations created, cassette mutagenesis will be used with degenerate pools of oligonucleotides (Hill et al., 1987). The mutagenesis program will be conducted in two stages: testing mutations near to, and mutations further from the catalytic amino acid identified. Initially, the identified catalytic amino acid will not be altered. When useful alterations of the active site are defined, mutagenesis of the catalytic amino acid will also be attempted. Two pools of degenerate oligonucleotides will be synthesized so that the 3' ends of one pool will hybridize with the 3' ends of the other pool and also come together to create a restriction site when annealed. The partial hybrids will be extended with the Klenow fragment of DNA polymerase 1 to form blunt-ended double-standard DNA, digested into dimers with the appropriate restriction enzyme and ligated into the α-glucosidase expression clone in place of the original active site sequence.

Instead of assaying the liquid cultures of individual clones, it will be possible to assay much greater numbers by an in situ assay. α-Glucosidase is active on PVDF membranes, provided that the membrane is kept moist. Lifts of replica-plated colonies on PVDF filters will be lysed and assayed by immersing the membrane in maltose and staining. The method is commonly used to test enzyme preparations. The cassette mutagenesis method employed should not reproduce the wild type. Thus, all positives should be mutants.

Colonies selected by this screening will then be grown in 5 ml cultures for the second round of screening. Aliquots will be lysed and assayed in two substrates—1) maltose, to assess efficiency with the 'preferred' substrate, and 2) a mixture of disaccharides with linkages other than α-1,4 to assess altered substrate specificity. These substrates will include trehalose and isomaltose. All clones that display a potentially valuable phenotype will be sequenced through the altered active site to determine which amino acids have been substituted.

We claim:

1. An isolated and purified sample of DNA, the DNA comprising a DNA sequence coding for barley α-glucosidase, SEQ ID NO: 4.

2. A vector containing a DNA sequence of claim 1.

3. A microbial host transformed by a vector of claim 2.

4. The isolated and purified DNA of claim 1 wherein the DNA is SEQ ID NO: 3.

5. A DNA construct comprising SEQ ID NO: 3.

6. A DNA construct comprising:
   a. a DNA sequence coding for barley α-glucosidase, SEQ ID NO: 4;
   b. a promoter located 5' to the DNA coding sequence; and
   c. a 3' termination sequence.

7. A method for the preparation of barley α-glucosidase, the method comprising the steps of:
   a. culturing a host transformed with a genetic construction including a coding sequence for barley α-glucosidase, SEQ ID NO: 4 under conditions suitable for the expression of the genetic construction; and
   b. recovering the barley α-glucosidase from the culture.

* * * * *